(12) United States Patent
Camisani et al.

(10) Patent No.: US 11,766,508 B2
(45) Date of Patent: Sep. 26, 2023

(54) BIOPROCESSING SYSTEM

(71) Applicant: Biosafe S.A., Eysins (CH)

(72) Inventors: Julien Camisani, Eysins (CH); Pau Mato Sabat, Eysins (CH)

(73) Assignee: Biosafe S.A., Eysins (CH)

( * ) Notice: Subject to any disclaimer, the term of this patent is extended or adjusted under 35 U.S.C. 154(b) by 339 days.

(21) Appl. No.: 16/767,403

(22) PCT Filed: Dec. 6, 2018

(86) PCT No.: PCT/EP2018/083882
§ 371 (c)(1),
(2) Date: May 27, 2020

(87) PCT Pub. No.: WO2019/110767
PCT Pub. Date: Jun. 13, 2019

(65) Prior Publication Data
US 2020/0368411 A1    Nov. 26, 2020

(30) Foreign Application Priority Data
Dec. 7, 2017 (GB) ...................... 1720405

(51) Int. Cl.
*A61M 1/02* (2006.01)
*B01D 21/26* (2006.01)
(Continued)

(52) U.S. Cl.
CPC .......... *A61M 1/0209* (2013.01); *A61M 1/025* (2013.01); *A61M 1/0272* (2013.01);
(Continued)

(58) Field of Classification Search
CPC .. A61M 1/0209; A61M 1/025; A61M 1/0272; A61M 2202/0413;
(Continued)

(56) References Cited

U.S. PATENT DOCUMENTS 5,690,835 A    11/1997  Brown
6,335,166 B1*   1/2002  Ammann ................ B01F 29/30
                                                    435/6.12
(Continued)

FOREIGN PATENT DOCUMENTS

CN       1331610 A     1/2002
CN     103948467 A     7/2014
(Continued)

OTHER PUBLICATIONS

PCT International Search Report and Written Opinion for PCT Application No. PCT/EP2018/083882 dated Jul. 23, 2019 (18 pages).

(Continued)

*Primary Examiner* — Joseph W Drodge
(74) *Attorney, Agent, or Firm* — Eversheds Sutherland (US) LLP (57) ABSTRACT

Disclosed is a bioprocessing system comprising apparatus (200) including a centrifugal separation housing (210) having a temperature controllable compartment (215) for removably accepting a separation chamber (50), the apparatus further comprising at least one mixing station (250) for supporting one or more fluid storage vessels (10, 20, 30, 40), the station including a temperature controllable area (252) for increasing or decreasing the temperature of the contents of the or each supported vessel. The system further includes a disposable fluidic arrangement (100) including a centrifugal separation chamber (50) removably mountable within the compartment (215) and having one or more ports (52) allowing fluid ingress into, or egress out of the chamber, via the one or more ports in use, said ports being in fluid communication with one or more of said fluid storage vessels via fluid conduits (12, 22, 32, 42) and via one or more valve arrangement.

12 Claims, 2 Drawing Sheets

(51) Int. Cl.
*B01D 21/30* (2006.01)
*B01D 21/34* (2006.01)
*B04B 5/04* (2006.01)
*B04B 15/02* (2006.01)
*B04B 13/00* (2006.01)

(52) U.S. Cl.
CPC ......... *B01D 21/262* (2013.01); *B01D 21/302* (2013.01); *B01D 21/34* (2013.01); *B04B 5/0442* (2013.01); *B04B 13/00* (2013.01); *B04B 15/02* (2013.01); *A61M 2202/0413* (2013.01); *A61M 2205/3372* (2013.01); *A61M 2205/3673* (2013.01)

(58) Field of Classification Search
CPC .. A61M 2205/3372; A61M 2205/3673; A61M 1/3692; A61M 1/3698; A61M 2202/0415; A61M 2202/0427; A61M 2202/0429; A61M 2202/0437; A61M 2202/0439; A61M 2205/3368; A61M 1/0281; A61M 1/369; A61M 1/029; A61M 1/3623; A61M 1/3693; A61M 1/3696; A61M 2205/3633; B01D 21/302; B01D 21/34; B01D 21/262; B04B 5/0442; B04B 13/00; B04B 15/02; B04B 2005/0485; B04B 5/0485; B04B 11/02; B04B 11/04; C12M 1/264; C12M 1/38; C12M 33/10; C12M 41/12; C12M 45/05; B01F 29/10; B01F 29/15; B01F 31/23; B01F 35/2115; B01F 35/2215
See application file for complete search history.

(56) References Cited

U.S. PATENT DOCUMENTS

| | | | | |
|---|---|---|---|---|
| 6,416,454 | B1* | 7/2002 | Kessler | B04B 15/02 494/13 |
| 2002/0128584 | A1 | 9/2002 | Brown et al. | |
| 2002/0133002 | A1* | 9/2002 | Heath | G01N 1/40 536/25.4 |
| 2002/0147787 | A1 | 10/2002 | Littlefield | |
| 2004/0092731 | A1* | 5/2004 | Heath | B01L 3/50825 536/25.4 |
| 2005/0009680 | A1* | 1/2005 | Sacco, Jr. | B04B 5/0442 494/37 |
| 2006/0083720 | A1 | 4/2006 | Fraser et al. | |
| 2010/0279405 | A1 | 11/2010 | Peterson et al. | |
| 2010/0311559 | A1 | 12/2010 | Miltenyi et al. | |
| 2011/0294640 | A1 | 12/2011 | Dolecek | |
| 2013/0130369 | A1* | 5/2013 | Wilson | G01F 23/26 435/289.1 |
| 2015/0056691 | A1 | 2/2015 | Stubbers et al. | |
| 2015/0104796 | A1* | 4/2015 | Goemann-Thoss | G01N 35/0092 435/6.12 |
| 2017/0045542 | A1* | 2/2017 | Lapham | G01N 35/00584 |
| 2017/0177913 | A1* | 6/2017 | Benedetti | G06K 7/10366 |
| 2018/0010990 | A1* | 1/2018 | Cherubini | B01L 3/5021 |

FOREIGN PATENT DOCUMENTS

| | | |
|---|---|---|
| CN | 105745545 A | 7/2016 |
| CN | 107078362 A | 8/2017 |
| CN | 107106744 A | 8/2017 |
| EP | 3151970 B1 | 8/2018 |
| GB | 2006058 A | 5/1979 |
| JP | 2004535216 A | 11/2004 |
| JP | 2009226174 A | 8/2009 |
| JP | 2011505890 A | 3/2011 |
| KR | 10-2001-0099952 A | 11/2001 |
| WO | 2000038762 A1 | 7/2000 |
| WO | 02070033 A2 | 9/2002 |
| WO | 2003/053346 A2 | 7/2003 |
| WO | 2005/012480 A2 | 2/2005 |
| WO | 2009072003 A3 | 6/2009 |
| WO | 2011/149614 A1 | 12/2011 |
| WO | 2015186057 A1 | 12/2015 |

OTHER PUBLICATIONS

Great Britain Search Report for GB Application No. 1720405.8 dated May 4, 2018 (4 pages).
Great Britain Search Report for GB Application No. 1720405.8 dated Nov. 28, 2018 (2 pages).
Office Action Issued in Japanese Application No. 2020-531085, dated Oct. 3, 2022 with English Translation (13 pages).
Office Action Issued in Chinese Patent Application No. 201880078957.4, dated Sep. 22, 2022 with English Translation (18 pages).
Search Report Issued in Chinese Patent Application No. 201880078957.4, dated Sep. 9, 2022 (6 pages).
Korean Preliminary Notice of Final Rejection for KR Application No. 10-2020-7019158, dated May 10, 2023 (32 pages).

* cited by examiner

BIOPROCESSING SYSTEM

CROSS REFERENCE TO RELATED APPLICATIONS

This application claims the priority benefit of PCT/EP2018/083882 filed on Dec. 6, 2018, which claims priority benefit of Great Britain Patent Application No. 1720405.8 filed on Dec. 7, 2017, the entire contents of which are hereby incorporated by reference herein.

FIELD OF THE INVENTION

The present invention relates to a bioprocessing system, in particular to a bioprocessing system which allows for selective multiple functionality in bioprocessing. For example the separation of fluids such as cell suspensions into their component parts, the maintaining or changing of the temperature of cell suspensions, the mixing of cell suspensions or their component parts, the storage of cell suspensions in storage vessels, and the readying for cell suspensions for further processing.

BACKGROUND OF THE INVENTION

It is known to process biological fluids such as separating of whole blood, apheresis blood, or bone marrow blood into red blood cells, white blood cells, platelets and plasma, and to separate suspensions of cells for example or stem cells expanded in number through culturing techniques and/or to separate certain cell populations like hematopoietic stem cells from other cells. In particular, blood separation systems and methods have emerged over the past 20 years in response to the growing need for efficient blood component therapies, which require the separation of stem cells from remaining blood components, for immediate use, for genetic modification and then their use, or storage for later use, for example after chemotherapy.

In a typical separation process, the components of blood, i.e. red blood cells, white blood cells, platelets and plasma are used for different therapies and therefore a certain amount of blood is processed in order to separate out these components. The blood is collected into a blood collection bag containing an anticoagulant solution. The collected blood is separated into its sub-components by spinning the blood bag for a period of about 10 minutes in a large refrigerated centrifuge. Following centrifugation, each of the components are expressed sequentially from the blood collection bag into separate collection bags.

There has been a desire for more automated, compact and portable systems for collection and separation of biological fluids, that are suitable even for processing relatively small volumes.

U.S. Pat. Nos. 3,737,096 and 4,303,193 propose a relatively small centrifugal apparatus attached to collapsible bags. However, these devices have a minimum fixed holding volume which requires a minimum volume usually of about 250 mL to be processed before any components can be collected.

U.S. Pat. No. 5,316,540 discloses a centrifugal processing where the processing chamber is a flexible processing bag which can be deformed hydraulically to fill it with biological fluid or empty it.

EP0654669-A discloses a centrifugal processing apparatus having two chambers separated by a piston. Before centrifugation, a small quantity of fluid to be processed is taken in via an off-centre inlet, and is transferred between the two chambers during centrifugal processing.

A functionally closed system for the separation blood constituents is described in U.S. Pat. Nos. 6,123,655 and 6,733,433 the contents of which are incorporated herein by reference. U.S. Pat. No. 6,123,655 teaches a portable and disposable centrifugal apparatus with a processing chamber of variable volume. It can therefore process a variable quantity of biological fluid, even down to very small quantities. U.S. Pat. No. 6,733,433 describes a similar apparatus. Both of these documents teach control of the movement of a sliding piston by means of a pneumatic system located at the bottom of the chamber that selectively creates either a vacuum or a positive pressure to move the piston up or down as desired.

Those patents propose a system for the processing and separation of biological fluids into components, comprising a set of containers for receiving the biological fluid to be separated and the separated components, and optionally one or more additional containers for additive solutions. A hollow centrifuge processing chamber is rotatable about an axis of rotation by engagement of the processing chamber with a rotary drive unit. The processing chamber has an axial inlet/outlet for biological fluid to be processed and for processed components of the biological fluid. This inlet/outlet leads into a separation space of variable volume wherein the entire centrifugal processing of biological fluid takes place. The processing chamber comprises a generally cylindrical wall extending from an end wall of the processing chamber, this generally cylindrical wall defines therein the hollow processing chamber which occupies a hollow open cylindrical space coaxial with the axis of rotation, the axial inlet/outlet being provided in said end wall coaxial with the generally cylindrical wall to open into the hollow processing chamber. The processing chamber contains within the generally cylindrical wall an axially movable piston. The separation space of variable volume is defined in an upper part of the processing chamber by the generally cylindrical wall and by the piston in the processing chamber. The separation space is in fluid communication with the inlet/outlet. Axial movement of the movable member varies the volume of the separation space, to introduce or expel a selected quantity of biological fluid to be processed into or out of the separation space via the inlet/outlet before, during or after centrifugal processing and to express processed biological fluid components from the separation space via the outlet during or after centrifugal processing.

The piston is operable to vary the separation space by means of a pneumatic pressure differential on the side of the piston opposite to the separation space, which is a generally closed volume. Clean air is pumped into or out of this closed volume to induce movement of the piston to vary the separation space volume and in turn to induce fluid flow into or out of the separation space.

Whilst this mechanism works well, the inventors have realised that therapeutic knowledge has advanced such that bioprocessing apparatus including a separation chamber but with more functionality is desirable. The increase in promising autologous and allogeneic cell therapies using different types of cells for development, for example hematopoietic, mesenchymal stromal, or progenitor dictates that a more versatile cell bioprocessing apparatus is needed. In addition the maintenance of sterility, in other words, keeping bioburden within acceptable limits or within limits specified by good manufacturing practice (GMP), is an imperative. Further, the costs of processing and costs of the equipment used for the processing is important too for the successful adoption and implementation of the relatively new therapies mentioned immediately above. Embodiments of the present invention address the shortcomings in the functionality of the prior art mentioned above, whilst addressing sterility and low cost.

SUMMARY OF THE INVENTION

According to one aspect the invention provides a bioprocessing system comprising apparatus including a housing having a temperature controllable compartment for removably accepting a separation chamber, the apparatus further comprising at least one station for supporting one or more fluid storage vessels, the station including a temperature controllable area for increasing or decreasing the temperature of the contents of the or each supported vessel.

In an embodiment the housing includes a rotational arrangement for centrifugal separation. In an embodiment the station comprises a table for said supporting, the table being moveable sufficiently to provide a mixing action in use. In an embodiment said movement is a cyclic rocking motion about at least one rotational axis and preferably two rotational axes. In an embodiment said table includes a hingeable and closable cover. In an embodiment the system further includes valve actuators for controlling the operation of one or more valves. In an embodiment the system further includes a controller and a temperature sensor for sensing the temperature at said compartment and at said area, and operable to heat or cool the compartment and/or the area, in response to said sensed temperature.

According to a second aspect the invention provides a system according to the above aspect when used with a disposable fluidic arrangement including a centrifugal separation chamber removably mountable within the compartment and having one or more ports allowing fluid ingress into, or egress out of the chamber, via the one or more ports in use, said ports being in fluid communication via fluid conduits and one or more valve arrangements with one or more of said fluid storage vessels. The disposable fluidic arrangement can be fluidically isolated from the remainder of the system for example to maintain sterility.

According to a third aspect the invention provides a method for the bioprocessing of fluids, the method comprising the following steps in any suitable order:
a) providing a bioprocessing system including a separation chamber in fluid communication with one or more fluid vessels,
b) introducing a cell suspension, such as mammalian cells into the separation chamber of the system;
c) controlling the temperature of the suspension;
d) introducing a further fluid or fluids into one or more fluid vessels of the system;
e) controlling the temperature of the further fluid(s) in said vessel(s) in relation to the temperature of the suspension; and
f) introducing at least a portion of the further fluids into the separation chamber at the same or a similar temperature as the suspension.

According to a fourth aspect the invention provides a method for the bioprocessing of cell suspensions to provide any one or more of: cell washing; cell separation and/or concentration; cell incubation; cell transduction; density gradient media cell separation; cell dilution; cell dispensing; and final formulation; the method comprising the steps of:
a) providing a bioprocessing system according to any one of the preceding claims; and
b) operating the system according to any one or more of the procedures defined in the examples 1 to 8 described herein.

The invention encompasses cells obtained by any one of the methods mentioned above.

Thus, as well as separation or other bioprocessing of fluids the invention allows heating, cooling, or maintenance of a generally constant temperature of fluids for example a human biological fluid in the separation chamber and a biological reagent stored separately in a bag to reduce or eliminate thermal shock when the two fluids are combined.

Where the apparatus is used for cell manipulation in multiple steps, for example sequential steps such as sedimentation, incubation, and mixing with reagent, temperature control can be assured, for example for quality control proposes. In addition to the above method steps, the cells may be subjected to one or more of washing, incubation, transduction, separation, density gradient separation, concentration adjustment, or mixing, with the aid of said further fluids where appropriate.

Where processing of cells or other contents of the separation chamber result in a change in temperature, typically a heat gain as a result of friction within the chamber generated by the centrifugation physical principle where a centrifugal separation principle is used, additional fluids can be introduced into the chamber at a lower (or higher) temperature, in order the adjust quickly the temperature in the chamber. Thereby the further fluids can be used to regulate the temperature of the fluids in the chamber rather than being introduced at the same temperature.

Further aspects and preferred features of the invention are recited in the claims. Even though the claims recite such aspects and preferred features, the invention is not limited to the claims and may extend to any features described herein, whether or not such features are mentioned in combination.

BRIEF DESCRIPTION OF THE DRAWINGS

The invention will be further described by way of example with reference to the accompanying drawings, wherein.

Figure 1:
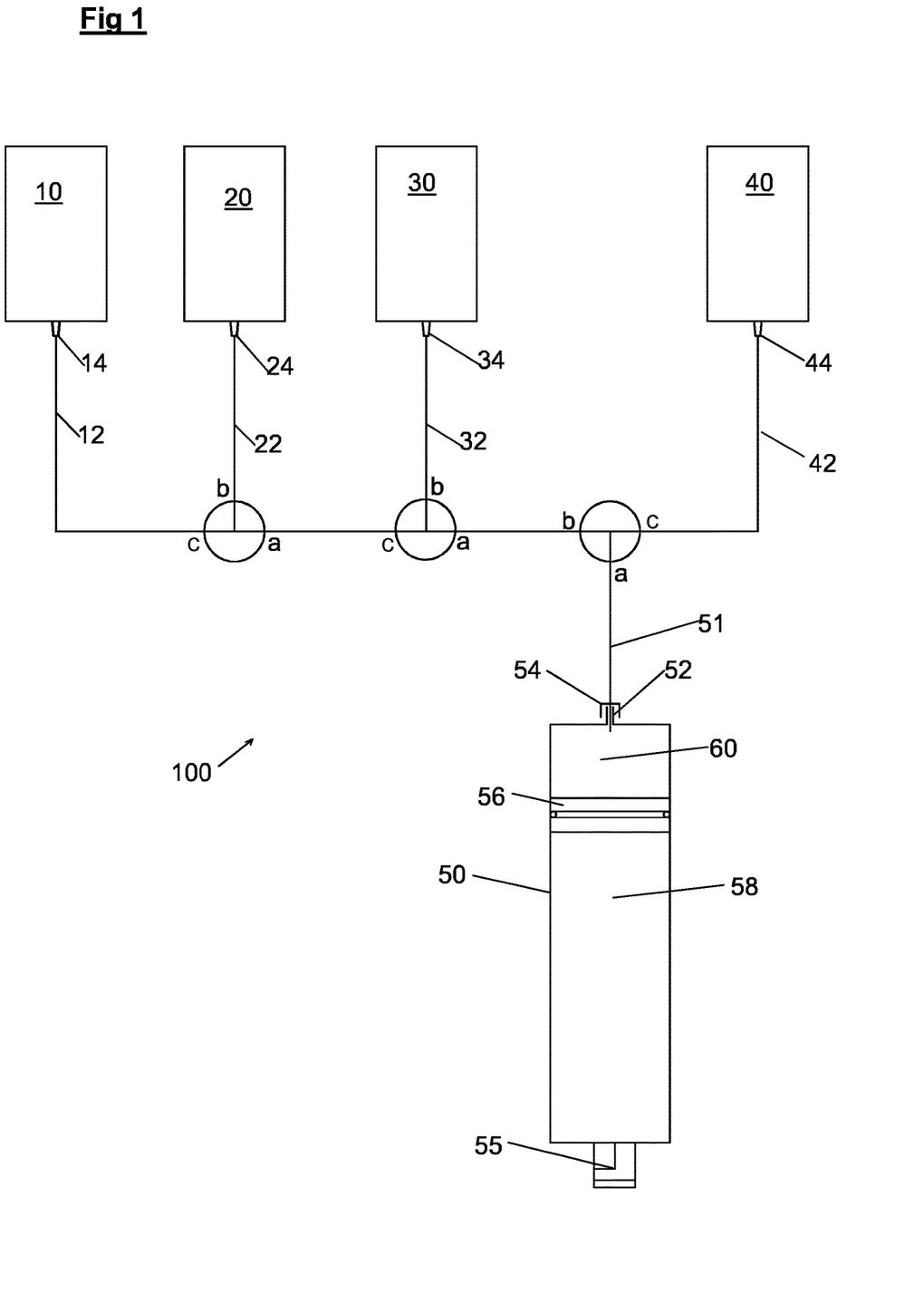
FIG. 1 shows schematically a closed fluidic disposable arrangement for bioprocessing.

With reference to FIG. 1, there is shown a disposable fluidic arrangement 100 comprising plural storage vessels 10, 20, 30, and 40, in this case in the form of flexible bags, for example HDPE plastics bags, each connectable to a respective fluid conduit 12, 22, 32, 42 via a fluid coupling 14, 24, 34, 44. Each fluid conduit 12, 22, 32, 42 is independently and selectively connectable to a process chamber 50, by the selective operation of, in this case, 2 way selection valves 16, 26, 36, providing selective connection of the ports a to c, or a to b, or no passage for fluids between the ports a, b and c of each valve. In this way any one of the bags 10 20 30 or 40, or any fewer or larger number of bags connected by a similar arrangement, can be selectively fluidically interconnected to the processing chamber 50 via respective fluid conduits.

The processing chamber 50 is a separation chamber, in this case a centrifugal separator having a static inlet port 52 which has a rotary coupling 54 allowing rotation of the chamber 50 at the same time as a sealed fluid connection to the stationary inlet port 52 and a stationary fluid conduit 51 which feeds the chamber and provides the fluid communication to the bags 10, 20, 30 and 40.

The chamber 50 has a piston 56 including a sliding seal, which is moveable by means of a pressure differential in a volume 58 on the distal side of the piston 56 compared to a volume 60 on the proximal side of the piston 56. By pumping or sucking gases or fluids, for example filtered air into or out of the distal volume 58, via a control port 55 it is possible to control the movement of the piston 56 and thereby to control the ingress or egress of fluids into or out of the processing chamber volume 60. Further control of the valves 16, 26 and 36 allows the selective introduction of fluids into the chamber volume 60 or vice versa.

Whilst the above fluidic arrangement would perform in a satisfactory manner, for example for separating blood constituents, where increased functionality is needed, further refinements are desirable.

Figure 2:
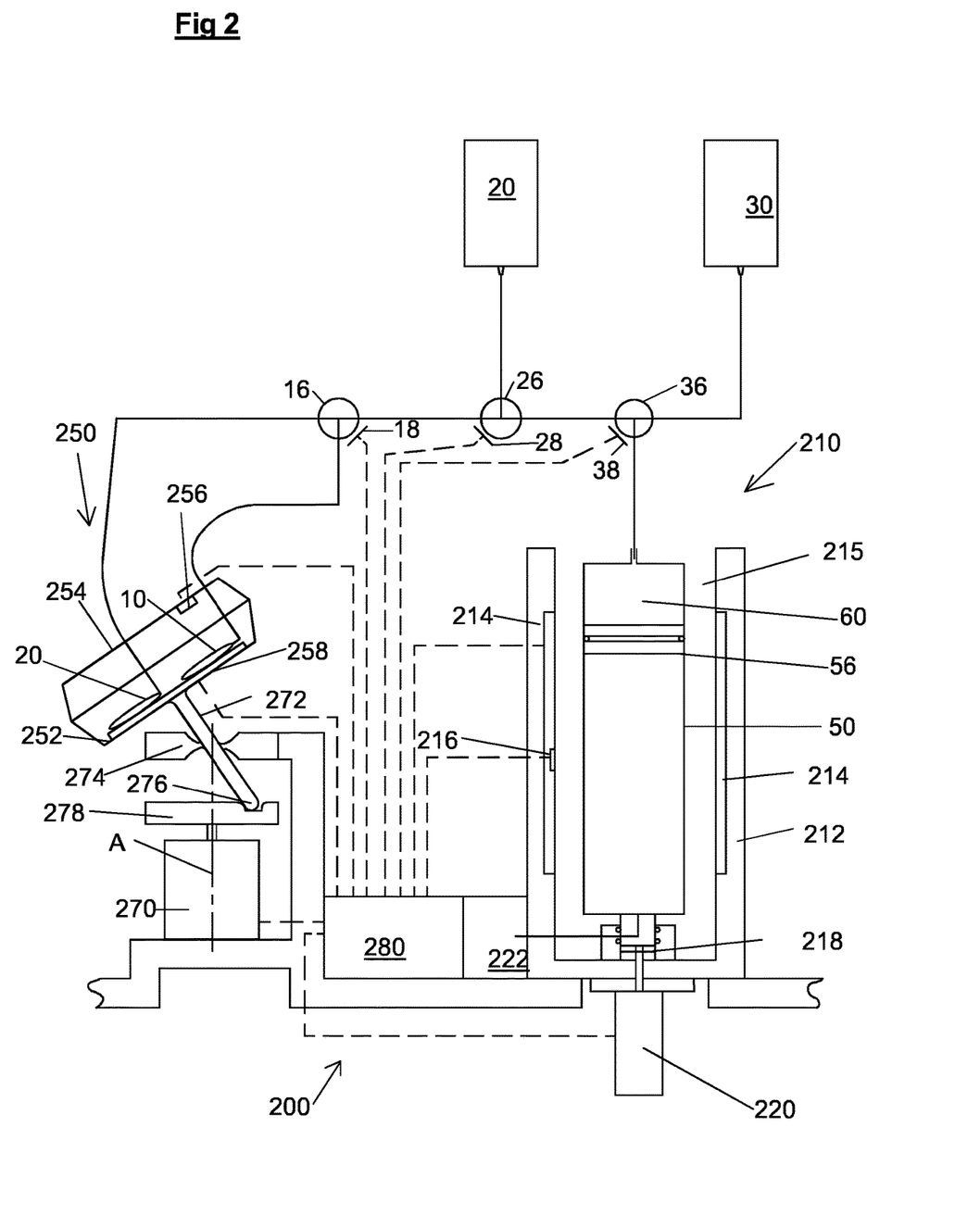
FIG. 2 shows the fluidic arrange of FIG. 1 together with apparatus used for multiple selective bioprocessing functions.

Referring additionally to FIG. 2 the disposable fluidic arrangement 100 is shown in situ in bioprocessing apparatus 200. When the arrangement 100 and apparatus are employed together they form a bioprocessing system. The apparatus 200 includes a temperature controlled centrifuge 210 and a temperature controlled mixing stage 250 as well as a controller 280. The apparatus has valve actuators 18, 28 and 38 to actuate the above mentioned valves, for example, each in the form of a rotatable boss which connects to the rotor of a respective valve to move the rotor selectively into a position which provides a desired fluid path.

The centrifuge has an insulated housing 212, including a compartment 215 which accepts the chamber 50. The housing has a Peltier element 214 for heating and cooling of the inside of the compartment, which in turn heats or cools the chamber 50 and its contents in use The temperature is controlled by the controller 280 and is measured by an infrared temperature sensor 216 providing feedback to the controller 280. The housing 210 further includes at a lower end a drive dog 218 rotatable connected to a drive motor 220 and a pneumatic feed pneumatically connected to an air pump 222, which together spin the chamber 50 in use to separate the constituents of fluids in the chamber, and control the movement of the poison 56 in the chamber 50, to provide fluid flow into or out of the chamber volume 60 for example to sequentially remove separated constituents routed to one or more of the bags, all under the control of the controller 280.

The mixer station 250 includes a table 252 which can support one or more of the flexible bags, in this case bags 10 and 20 which remain in fluid communication with the remainder of the arrangement 100. The table is rockable under the influence of a mixer motor 270 and related mixing mechanism to promote mixing of the contents of the bags. In this case the mechanism includes a stem 272 rigidly depending from the table 252, the stem 272 being supported at a middle portion by a flexible support 274, and being driven in use a circular motion at a distal end 276 by a wheel 278 mounted to the mixer motor 270. The mixer mechanism allows the table to roll in two axes each perpendicular to the axis of rotation A of the mixer motor 270. Other suitable mixing mechanisms could be employed.

The mixer stage includes also a hinged lid 254 to close over the bags to reduce heat loses. A Peltier element 258 for heating or cooling the bags 10 and 20 and an infrared temperature sensor 256 are provided also, each under the control of the controller 280.

It will be evident that the temperature controlled mixer 250 increases the functionality of the apparatus 200, and specific examples of the increased functionality are given below. The flexible bags 10-40 and the volume 60 each have a capacity of about 10 ml to about 1000 ml, which means that embodiments of this apparatus are portable and the fluidic arrangement 100, including the separation chamber 50 can be made readily disposable or single use. Thermal shock can be reduced or eliminated by making the contents of any of the bags 10, 20, 30 or 40 introduced into the mixer 250 the same or similar to the temperature of fluids in the volume 60 when they are combined (not necessarily in the volume 60). That functionality is particularly useful for biological additives introduced into blood products.

The apparatus has the ability to control the temperature of mammalian, for example human, biological fluid processed, such as whole blood, apheresis blood, bone marrow blood or expanded cells or stem cells through culturing techniques in combination with the addition, mixing, dilution or resuspension with any other biological reagents such a washing solution, suspension medium, human or fetal serum, gradient density solution, affinity particles such as magnetic beads, virus suspended in a medium solution or cryoprotectant solution such as dimethylsulfoxide (DMSO) among others, all manipulated by the system described above.

BIOPROCESSING EXAMPLES

By way of example some bioprocessing procedures are given below which may be performed using the system described above. It will be appreciated that the procedures require a control function, which in practice is performed by controller 280, controlling the mixer arrangement 250, the valves 16, 26 and 36 and the centrifuge separation chamber 210.

Example 1—Cell Washing Procedure a) introducing to a bag, for example bag 10, a cell-based product such as cultured stem cells suspended in a fluid;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring the temperature of the product in the volume 60 (typically 4 degrees Celsius);
e) introducing into a bag, for example bag 20, a cell washing solution;
f) connecting the bag to the remainder of the disposable fluidic arrangement 100 via the fluid coupling 24;
g) introducing the filled bag 20 into the mixing arrangement 250, optionally mixing the washing solution, measuring the temperature of the washing solution and, while the bag is within the mixing arrangement 250, adjusting the temperature of the washing solution to be the same or similar to the temperature of the product in the volume 60;
h) following step g) introducing the washing solution into the volume 60 which already contains the product, in this case by means of further moving the piston 56;
i) spinning the volume 60 for a sufficient time and with sufficient rotational velocity or acceleration to substantially separate cells in the product from less dense materials including the washing solution;
j) transferring the washing solution together with the less dense materials of the cell product from the volume 60 and into a bag, for example bag 30, in this case by means of opposite movement of the piston 56; and k) transferring the residual fluid material, including washed cells from the volume into a bag, from example bag 40, in this case by means of further opposite movement of the piston 56.

Example 2—Cell Separation and/or Concentration Procedure a) introducing to a bag, for example bag 10, a cell-based product such as cultured stem cells suspended in a fluid;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring the temperature of the product in the volume 60 (typically at 4 degrees Celsius);
e) spinning the volume 60 for a sufficient time and with sufficient rotational velocity or acceleration to substantially separate the majority of suspended cells in the product from less dense materials in the product and optionally controlling the temperature of the cells in the volume, for example by maintaining said temperature during at least a period in this step and optionally in the preceding steps (typically at 4 degrees Celsius);
f) transferring the less dense materials of the cell product from the volume 60 and into a bag, for example bag 30, in this case by means of opposite movement of the piston 56; and
g) transferring the residual fluid material, including the now separated and/or concentrated cells from the volume into a bag, from example bag 40, in this case by means of further opposite movement of the piston 56.

Example 3—Cell Incubation Procedure a) introducing to a bag, for example bag 10, a cell-based product such as stem cells suspended in a fluid;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring the temperature of the product in the volume 60 (typically initially at room temperature) and adjusting the product's temperature to around 37 degrees Celsius if necessary;
e) introducing into a bag, for example bag 20, a multiplicity of cell incubation beads suspended in a solution and adapted to bind to said cells;
f) connecting the bag to the remainder of the disposable fluidic arrangement 100 via the fluid coupling 24;
g) optionally introducing the filled bag 20 into the mixing arrangement 250, optionally mixing the incubation beads, measuring the temperature of the beads and, while the bag 20 is within the mixing arrangement 250, adjusting the temperature of the beads to be the same or similar to the temperature of the product in the volume 60;
h) following step g) introducing the beads into the volume 60 which already contains the product, in this case by means of further moving the piston 56, or in the alternative introducing the cells in volume 60 into the bag 20 containing the beads;
i) maintaining the temperature of the combined suspension of cell product and beads, for example, in the volume 60 or in the bag 20;
j) transferring said suspension, including beads, from the volume or bag 20 and into another bag, for example bag 30, in this case by means of movement of the piston 56 in order to perfuse the cells and optionally transferring the combined suspension back into the volume;
k) optionally repeating step j) once or more than once;
l) spinning the volume 60 for a sufficient time and with sufficient rotational velocity or acceleration to substantially separate the majority of suspended cells bound to said beads from less dense materials in the combined suspension
m) transferring the less dense materials of the now separated suspension from the volume 60 and into a bag, for example bag 30, in this case by means of opposite movement of the piston 56; and
g) transferring the residual fluid material, including the now incubated cells from the volume into a bag, from example bag 40, in this case by means of further opposite movement of the piston 56.

Example 4 Cell Transduction Procedure a) introducing to a bag, for example bag 10, a cell-based product such as cultured stem cells suspended in a fluid;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the product, or mixed product from the bag to the processing chamber volume 60 in the manner described above, in this case by means of moving the piston 56 to draw in the cell product, measuring the temperature of the product in the volume 60 (typically 4 degrees Celsius), and optionally adjusting the temperature of the suspension in the volume, for example to between room temperature and 37 degrees Celsius;
e) introducing into a bag, for example bag 20, a transduction agent such as a virus; f) connecting the bag to the remainder of the disposable fluidic arrangement 100 via the fluid coupling 24;
g) introducing the filled bag 20 into the mixing arrangement 250, optionally mixing the washing solution, measuring the temperature of the washing solution and, while the bag is within the mixing arrangement 250, adjusting the temperature of the transduction agent to be the same or similar to the temperature of the product in the volume 60;
h) following step g) introducing the transduction agent into the volume 60 which already contains the product, in this case by means of further moving the piston 56;
i) spinning the volume 60 for a sufficient time and with sufficient rotational velocity or acceleration to substantially effect transduction of the transduction agent into the product, and allowing the transduction to take place;
j) further spinning the volume 60 for a sufficient time and with sufficient rotational velocity or acceleration to separate transduced cells in the product from less dense materials including the remainder of the transduction agent suspension;

k) transferring the less dense materials from the volume 60 and into a bag, for example bag 30, in this case by means of opposite movement of the piston 56; and
l) transferring the residual fluid material, including transduced cells from the volume into a bag, from example bag 40, in this case by means of further opposite movement of the piston 56.

In the above example, transduction can also be done while cells are in a bag, for example bag 10.

Example 5—Density Gradient Separation Procedure a) introducing into a bag, for example bag 10, density gradient media;
b) connecting the bag 10 to the remainder of the disposable fluidic arrangement 100 via the fluid coupling 14;
c) transferring the contents of the bag 10 into the separation chamber volume 60, and optionally adjusting temperature of the density gradient media in the volume for example to between room temperature and 37 degrees Celsius.
d) introducing to a bag, for example bag 20, a cell-based product such as cultured stem cells suspended in a fluid;
e) connecting the bag to the remainder of the disposable fluidic arrangement 100 via the fluid coupling 24;
f) optionally introducing the filled bag 20 into the mixing arrangement 250, optionally mixing the product, optionally measuring the temperature of the product, and optionally adjusting the temperature of the product to the same or similar to the temperature of the density gradient media in the volume 60;
g) spinning the volume 60 while transferring the mixed product from the bag to the volume 60 in the manner described above, in this case by means of moving the piston 56 to draw in the cell product at a rate which is slower than in the procedures mentioned above, and optionally maintaining the temperature of the media and product in the volume 60;
h) transferring a portion of the spun contents of the volume into a bag, for example bag 30, in this case by means of opposite movement of the piston 56; and
i) transferring the residual fluid material, including cells separated within the density gradient media from the volume into a bag, from example bag 40, in this case by means of further opposite movement of the piston 56.

Example 6—Cell Dilution or Cell Development Procedure a) introducing to a bag, for example bag 10, a cell-based product such as cultured stem cells suspended in a fluid having a known cell density;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring the temperature of the product in the volume 60 (typically 4 degrees Celsius);
e) introducing into a bag, for example bag 20, a cell dilution or cell development solution;
f) connecting the bag to the remainder of the disposable fluidic arrangement 100 via the fluid coupling 24;
g) introducing the filled bag 20 into the mixing arrangement 250, optionally mixing the dilution or development solution, measuring the temperature of the said solution and, while the bag 20 is within the mixing arrangement 250, adjusting the temperature of the solution to be the same or similar to the temperature of the product in the volume 60;
h) following step g) introducing the solution or only a portion of the solution into the volume 60 which already contains the product, in this case by means of further moving the piston 56, said portion being determined by the required dilution of the cell product;
i) optionally transferring the contents of the volume to a further bag 30, and back to the volume one or more times to encourage perfusion of the cells;
j) transferring the diluted cells from the volume into a bag, from example bag 40, in this case by means of further opposite movement of the piston 56.

Example 7—Measured Cell Volume Dispensing Procedure a) introducing to a bag, for example bag 10, a cell-based product such as cultured stem cells suspended in a fluid;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring and controlling the temperature of the product in the volume 60 (typically to be maintained between room temperature and 4 degrees Celsius);
e) transferring the product sequentially from the volume into one of more bags 20, 30 or 40, or other vessels to provide measured cell product aliquots.

Example 8—Cell Final Formulation Procedure a) introducing to a bag, for example bag 10, a cell-based product such as cultured stem cells suspended in a fluid having a known cell density;
b) connecting the bag to the remainder of the disposable fluidic arrangement 100 via the fluid coupling 14;
c) optionally introducing the filled bag 10 into the mixing arrangement 250, optionally mixing the product and optionally measuring the temperature of the product;
d) transferring the mixed product from the bag to the processing chamber volume 60 in the manner described above, in this case by means of moving the piston 56 to draw in the cell product, and measuring and adjusting the temperature of the product in the volume 60 (typically at 4 degrees Celsius);
e) introducing into a bag, for example bag 20, a cell cryoprotectant for example DMSO;
f) connecting the bag to the remainder of the disposable fluidic arrangement 100 via the fluid coupling 24;
g) introducing the filled bag 20 into the mixing arrangement 250, optionally mixing the cryoprotectant, measuring the temperature of the cryoprotectant and, while the bag 20 is within the mixing arrangement 250, adjusting the temperature of the cryoprotectant to be the same or similar to the temperature of the product in the volume 60;
h) following step g) introducing the cryoprotectant or only a portion of the cryoprotectant into the volume 60 which already contains the product, in this case by means of further moving the piston 56, said portion being determined by the required cryoprotectant dilution of the cell product;

i) spinning the volume 60 for a sufficient time and with sufficient rotational velocity or acceleration to substantially concentrate cells in the product into one part of the volume and to leave the remaining part having fewer cells;

j) transferring the part of the volume having fewer cells from the volume 60 and into a bag, for example bag 30, in this case by means of opposite movement of the piston 56; and k) transferring the residual fluid material, including a concentration of cells in the cryoprotectant from the volume into a bag, from example bag 40, in this case by means of further opposite movement of the piston 56.

It will be appreciated that the above procedures could be employed individually or in combination for example such that they are chained together, in which case it will be apparent that some of the initial steps and/or latter steps need not be repeated. Whilst it is not essential the preferred way to separate cells is to spin the volume and allow the heavier cells to be urged outwardly into an outer annular portion of the chamber. The relatively cell-sparse inner volume can be pushed out of the volume first by the piston followed by the relatively cell rich outer volume, and appropriate routing of the two distinct concentrations can be made to capture the cell rich fraction. Whilst compressed air is the preferred method of moving the piston, other motive force can be used. The disposable fluidic arrangement is shown having four bags only, but it will be appreciated that fewer or more bags or fluid receptacles may be employed, with other valve arrangements, for example suit the chained procedures mentioned above.

It will be appreciated that the above mentioned apparatus provides a versatile platform to perform the above mentioned procedure which are examples only of the bioprocessing procedures which are possible with the apparatus described. For example, the movement mechanism for the mixer 250 could be made more simple such that a single pivot axis could be used, or a gimble type arrangement could be used, where two axis rocking could be employed. Other mixing movements could be used also, for example linear movements. The valves used could be made more simple also, for example pinch valves could be used.

The scope of the invention is defined by the claims, and may include other examples that occur to those skilled in the art but not disclosed explicitly herein. Such other examples are intended to be within the scope of the claims if they have structural elements that do not differ from the literal language of the claims, or if they include equivalent structural elements with insubstantial differences from the literal language of the claims. Where features are described collectively, those features may be claimed separately without adding to the content of the invention as claimed, and conversely, where features are described separately, their combination in the claims is not intended to add material to the content of the invention as claimed. All patents and patent applications mentioned in the text are hereby incorporated by reference in their entireties, as if they were individually incorporated.

The invention claimed is:

1. A bioprocessing system comprising:
    an apparatus including a housing having a temperature controllable compartment for removably accepting a separation chamber, the apparatus further comprising at least one station for supporting one or more fluid storage vessels, the at least one station including a temperature controllable area for increasing or decreasing the temperature therein or of each supported vessel, and
    a controller and a temperature sensing system for sensing the temperature of both the temperature controllable compartment and the temperature controllable area, and operable to heat or cool the temperature controllable area, in response to said sensed temperature, wherein the temperature sensing system comprises a first sensor configured to sense the temperature of the temperature controllable compartment, and a second sensor configured to sense the temperature of the temperature controllable area;
    wherein the separation chamber is in fluid communication with the one or more fluid storage vessels, such that the separation chamber is configured to receive a fluid or fluids from the one or more fluid storage vessels at the same temperature as a cell suspension in the separation chamber; and
    wherein the housing comprises a Peltier element for heating and cooling of the temperature controllable compartment thereof, which is configured to accept the separation chamber therein.

2. A system according to claim 1, wherein the housing includes a rotational arrangement for centrifugal separation.

3. A system according to claim 1, wherein each of the at least one station comprises a table for said supporting, the table being moveable to provide a mixing action in use.

4. A system according to claim 3, wherein said movement is a cyclic rocking motion about at least one rotational axis.

5. A system according to claim 3, wherein the table includes a closable cover.

6. A system according to claim 1 further including valve actuators for controlling the operation of one or more valves, wherein the one or more valves are configured to be in fluid communication with the one or more fluid storage vessels.

7. A system according to claim 1, wherein said temperature sensors are contactless temperature sensors configured for sensing emitted infrared radiation.

8. A system according to claim 1 further comprising a disposable fluidic arrangement comprising a disposable separation chamber and one or more disposable fluid storage vessels in fluid communication with the disposable separation chamber, the disposable fluidic arrangement being separable, and fluidically isolated, from the apparatus.

9. A system according to claim 8 further comprising a centrifugal separation chamber removably mountable within the temperature controllable compartment and having one or more ports allowing fluid ingress into, or egress out of the separation chamber, via the one or more ports wherein the one or more ports are in fluid communication, via one or more fluid conduits, with one or more valves of the one or more fluid storage vessels.

10. A method for the bioprocessing of a cell suspension to provide any one or more of: cell washing; cell separation and/or concentration; cell incubation; cell transduction; density gradient media cell separation; cell dilution; cell dispensing; and final formulation; the method comprising the steps of:
    a) providing a bioprocessing system according to claim 1; and
    b) operating the bioprocessing system.

11. A method for the bioprocessing of fluids, the method comprising the following steps:
    a) providing a bioprocessing system including a housing comprising a temperature controllable compartment for removably accepting a separation chamber in fluid communication with one or more fluid vessels,
b) introducing a cell suspension, such as mammalian cells into the separation chamber of the system;
c) controlling the temperature of the suspension;
d) introducing a further fluid or fluids into said one or more fluid vessels of the system;
e) controlling the temperature of the further fluid or fluids in said one or more vessels based on the temperature of the suspension; and
f) introducing at least a portion of the further fluid or fluids into the separation chamber at the same temperature as the suspension;
wherein the housing comprises a Peltier element for heating and cooling the inside of the temperature controllable compartment thereof, which is configured to accept the separation chamber therein.

12. The method of claim 11, wherein the bioprocessing system further includes a station for mixing the further fluid or fluids introduced into one or more of said vessels, wherein the method further comprising the step of mixing the fluid or fluids introduced into the vessel or vessels at the mixing station and wherein step f) of claim 11 includes introducing at least a portion of the further fluid or fluids into the vessel or vessels at the mixing station, at the same temperature as the suspension being introduced into the separation chamber.

* * * * *